US008421044B2

(12) United States Patent
Mayfield et al.

(10) Patent No.: US 8,421,044 B2
(45) Date of Patent: Apr. 16, 2013

(54) RADIATION SHIELDING LID FOR AN AUXILIARY SHIELD ASSEMBLY OF A RADIOISOPTOPE ELUTION SYSTEM

(75) Inventors: Scott Hayward Mayfield, Florissant, MO (US); Kevin Robert Martz, Desoto, MO (US)

(73) Assignee: Mallinckrodt LLC, St. Louis, MO (US)

( * ) Notice: Subject to any disclaimer, the term of this patent is extended or adjusted under 35 U.S.C. 154(b) by 86 days.

(21) Appl. No.: 13/185,657

(22) Filed: Jul. 19, 2011

(65) Prior Publication Data

US 2012/0187316 A1 Jul. 26, 2012

Related U.S. Application Data

(63) Continuation-in-part of application No. 29/383,507, filed on Jan. 19, 2011, now Pat. No. Des. 657,886.

(51) Int. Cl.
*A61B 19/02* (2006.01)
*G21F 5/018* (2006.01)

(52) U.S. Cl.
USPC .................. 250/515.1; 250/496.1; 250/506.1; 250/507.1

(58) Field of Classification Search ............... 250/515.1, 250/496.1, 506.1, 507.1
See application file for complete search history.

(56) References Cited

U.S. PATENT DOCUMENTS

| | | | |
|---|---|---|---|
| D239,120 S | 3/1976 | Heyer et al. | |
| 5,582,315 A | 12/1996 | Reid | |
| D389,761 S | 1/1998 | Thomas | |
| D506,261 S | 6/2005 | Hellstom | |
| D589,157 S | 3/2009 | Speth | |
| D602,164 S | 10/2009 | Speth et al. | |
| D607,117 S | 12/2009 | Horton et al. | |
| D617,910 S | 6/2010 | Horton et al. | |
| 7,753,835 B2 * | 7/2010 | Van Der Lee et al. | 600/3 |
| 7,772,565 B2 * | 8/2010 | Wilson | 250/428 |
| D644,323 S | 8/2011 | Burgess et al. | |
| 8,003,967 B2 | 8/2011 | Fago et al. | |
| 2008/0197302 A1 | 8/2008 | Fago et al. | |
| 2012/0305429 A1 * | 12/2012 | Mayfield et al. | 206/438 |
| 2012/0305800 A1 * | 12/2012 | Mayfield et al. | 250/432 PD |

* cited by examiner

*Primary Examiner* — Nikita Wells
(74) *Attorney, Agent, or Firm* — Armstrong Teasdale LLP

(57) ABSTRACT

Disclosed herein are embodiments of a radiation shielding lid of a radiation shielding container (e.g., auxiliary radiation shield) designed to house a radioisotope generator assembly.

21 Claims, 11 Drawing Sheets

RADIATION SHIELDING LID FOR AN AUXILIARY SHIELD ASSEMBLY OF A RADIOISOPTOPE ELUTION SYSTEM

CROSS-REFERENCE TO RELATED APPLICATION

The present application is a continuation-in-part of U.S. patent application Ser. No. 29/383,507 filed Jan. 19, 2011, and having the title "Radiation Shielding Container Lid."

BACKGROUND

The present disclosure relates generally to a radiation shielding lid for an auxiliary shield assembly of a radioisotope elution system.

Nuclear medicine uses radioactive material for diagnostic and therapeutic purposes by injecting a patient with a dose of the radioactive material, which concentrates in certain organs or biological regions of the patient. Radioactive materials typically used for nuclear medicine include Technetium-99m, Indium-111, and Thallium-201 among others. Some chemical forms of radioactive materials naturally concentrate in a particular tissue, for example, radioiodine (I-131) concentrates in the thyroid. Radioactive materials are often combined with a tagging or organ-seeking agent, which targets the radioactive material for the desired organ or biologic region of the patient. These radioactive materials alone or in combination with a tagging agent are typically referred to as radiopharmaceuticals in the field of nuclear medicine. At relatively low doses of radiation from a radiopharmaceutical, a radiation imaging system (e.g., a gamma camera) may be utilized to provide an image of the organ or biological region in which the radiopharmaceutical localizes. Irregularities in the image are often indicative of a pathology, such as cancer. Higher doses of a radiopharmaceutical may be used to deliver a therapeutic dose of radiation directly to the pathologic tissue, such as cancer cells.

A variety of systems are used to generate, enclose, transport, dispense, and administer radiopharmaceuticals. One such system includes a radiopharmaceutical generator, including an elution column, and an input connector (e.g., an input needle) and an output connector (e.g., an output needle) in fluid communication with the elution column. Typically, a radiopharmacist or technician fluidly connects an eluant vial (e.g., a vial containing saline) to the input connector and fluidly connects an empty elution vial (e.g., a vial having at least a partial internal vacuum) to the output connector. The vacuum in the empty elution vial draws the eluant (e.g., saline) from the eluant vial through the elution column, and into the elution vial. The saline elutes radioisotopes as its flows through the elution column so that radioisotope-containing saline fills the elution vial. The elution vial is typically housed in its own radiation shielding container, sometimes referred to as an elution tool or an elution shield.

To reduce the amount of radiation exposure on the radiopharmacist or technician, the radiopharmaceutical generator is housed within a radiation shield assembly, sometimes referred to as an auxiliary shield, that includes a removable radiation shielding lid to allow the generator to be inserted into and removed from the shield assembly. The radiation shielding lid is disposed over the input connector and output connector of the generator, and includes an eluant opening and an eluate opening that are respectively aligned with the input connector and output connector of the generator and are sized and shaped for respectively receiving the eluant vial and the elution tool so that the respective vials can be fluidly connected to the input and output connectors. Although this type of system generally tends to work well, one problem associated with this type of system is that the input connector and/or output connector of the generator—particularly where the input and output connectors are hollow needles—may be bent, crushed, or broken due to misalignment of the eluant vial and/or the elution vial with the respective input and/or output connectors when making the fluid connection(s). As a result of the broken or deformed needles, the system operates less effectively or become completely useless. If the system contains radiopharmaceuticals, then the damaged connectors can result in monetary loss and/or delays with respect to nuclear medicine procedures. Another result of this misalignment problem can be that the input connector and/or output connector of the generator may undesirably puncture a retaining ring/collar of the respective eluant vial and/or elution vial causing damage to the vial(s).

This Background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

BRIEF SUMMARY

One aspect of this disclosure relates to a radiation shielding lid for a radiation shielding container that includes a body having an upper surface and an opposing lower surface. A vial opening is defined in the body of the lid. This vial opening has a lower end found at the lower surface of the body and an upper end intermediate the upper and lower surfaces of the body. A finger recess is defined in the upper surface of the body and is sized and shaped to allow at least a distal portion of each of at least two digits (e.g., thumb/fingers of a technician) to enter the finger recess. This finger recess has an upper edge adjacent the upper surface of the body and a lower edge adjacent the upper end of the vial opening. First and second wings extend upward from adjacent the upper end of the vial opening. Each of these first and second wings has opposite sides, a top portion, and an inner surface extending partially around a circumference of the upper end of the vial opening. The inner surfaces of the first and second wings and the vial opening together define a vial passageway extending from the top portion of each of the first and second wings through the lower surface of the body. The vial passageway is sized and shaped for receiving a vial therein. Respective adjacent sides of the first and second wings are spaced apart from one another around the vial opening to partially define first and second finger channels leading from the finger recess to the vial passageway. Each of the first and second finger channels are sized and shaped to allow at least the distal portion of each of at least two digits to enter the corresponding finger channel from the finger recess. One benefit of this arrangement may be to facilitate gripping of the vial during insertion of the vial into the vial passageway and/or removal of the vial from the vial passageway.

In some embodiments of the first aspect, the inner surface of each of the first and second wings extends at least 45 degrees and less than 180 degrees around the circumference of the upper end of the vial opening. The top portions of the first and second wings may extend above the upper surface of the body. The inner surface of each of the first and second wings may extend at least 60 degrees around the circumference of the upper end of the vial opening, or may extend at least 90 degrees around the circumference of the upper end of the vial opening. The inner surfaces of the first and second wings may be diametrically opposed to one another with respect the vial opening.

In some embodiments of the first aspect, the sides of the respective first and second wings extend into the finger recess. The finger recess may include first and second finger recesses, and the first and second finger recesses may be diametrically opposed to one another with respect to the vial opening. The lower edge of the first finger recess may extend between the corresponding adjacent sides of the first and second wings to partially define the first finger channel, and the lower edge of the second finger recess may extend between the corresponding adjacent sides of the first and second wings to partially define the second finger channel. The top portions of the first and second wings may extend above the upper surface of the body, and at least one of the first and second wings may have a notch in the corresponding top portion.

In some embodiments of the first aspect, the upper end of the vial opening may be substantially circular, and the inner surfaces of the first and second wings may be generally arcuate. A portion of the vial passageway defined by the inner surfaces of the wings may taper from the top portions of the wings toward the vial opening. Each of the first and second wings may include a plurality of ribs on the inner surface of each wing projecting inward into the vial passageway, and the ribs on each wing may be spaced apart from one another between the opposite sides of each wing. The ribs may project generally toward a centerline of the passageway from the inner surface of the corresponding wing, such that each rib has a terminal, guiding surface generally facing a centerline of the vial passageway, and each guiding surface may be uniformly spaced from the centerline of the vial passageway along its length. The body may be substantially disk-shaped and may be formed, at least in part, from a radiation shielding material including at least one of depleted uranium, tungsten, tungsten impregnated plastic, or lead. An elution tool opening may be defined in the body, and the elution tool opening may be spaced apart and separate from the vial opening.

A second aspect of this disclosure also relates to a lid for a radiation shielding container that includes a body having upper and lower surfaces. In this second aspect, a vial opening in the body has a centerline extending through the upper and lower surfaces of the body. The vial opening is sized and shaped to accommodate insertion of a vial therein and removal of the vial therefrom. First and second alignment wings extend upward from the vial opening. Each of these first and second alignment wings has opposite sides, a top portion, and an inner surface extending partially around a circumference of the vial opening. In some embodiment, the first and second alignment wings may be said to enable or promote alignment of a longitudinal axis of a vial with the centerline of the vial opening as the vial is inserted into the vial opening. Respective adjacent sides of the first and second alignment wings partially define at least one finger channel sized and shaped to allow at least a distal portion of at least one finger (e.g., a finder of a technician) to enter the finger channel. Such an arrangement may be found by users to facilitate insertion of the vial into and/or removal of the vial from the vial opening.

In some embodiments of the second aspect, the inner surface of each alignment wing extends at least 45 degrees and less than 180 degrees around the circumference of the vial opening, and the finger channel may include at least a first finger channel and a second finger channel. First and second finger recesses may be in the upper surface of the body. Each of the first and second finger recesses may have an upper edge adjacent the upper surface of the body and a lower edge leading to the vial opening. The first and second finger recesses may be diametrically opposed to one another with respect to the vial opening. An elution tool opening defined in the body may be spaced apart and separate from the vial opening.

Yet a third aspect of this disclosure also relates to a radiation shielding lid that includes a body having upper surface and an opposing lower surface. In this third aspect, the body of the lid includes at least one appropriate radiation shielding material (e.g., a material capable of shielding radiation emitted by medical radioisotopes (e.g., beta and/or gamma radiation)). Examples of such radiation shielding material include depleted uranium, tungsten, tungsten impregnated plastic, and lead. A first opening is defined in the body of the lid. This first opening has a lower end at the lower surface of the body and an upper end intermediate the upper and lower surfaces of the body. A second opening is also defined in the body of the lid. However, this second opening has a lower end at the lower surface of the body and an upper end at the upper surface of the body. The second opening is spaced apart and separate from the first opening. In addition, a recess is defined in the body of the lid. At least a portion of an upper end of this recess is located at the upper surface of the body, and at least a portion of a lower end of this recess is located at the upper end of the first opening. Further, first and second wings extend upward (e.g., away from the lower surface of the body) and only partially about a circumference of the upper end of the first opening such that a gap is defined between the first wing and the second wing.

In some embodiments of the third aspect, the first and second wings have top portions extending above the upper surface of the body. A diameter of the first opening may be less than a diameter of the second opening. The first and second wings may be diametrically opposed to one another with respect the first opening. The finger recess may include first and second recesses, and the first and second recesses may be diametrically opposed to one another with respect to the vial opening. The gaps may be diametrically aligned with the first and second recesses relative to the first opening. At least one of the first and second wings may have a notch in a top portion thereof.

Still a fourth aspect of this disclosure relates to a method of using a radiation shielding lid. In this method a first container having non-radioactive medical fluid (e.g., saline) therein is inserted into a first opening defined in and extending entirely through the radiation shielding lid. The insertion of the first container into the first opening includes the first container being passed between first and second opposing wings that extend away from a bottom of the lid upward beyond a top of the radiation shielding lid. A second container is inserted into a second opening defined in and extending entirely through the radiation shielding lid. This second opening is separate and distinct from the first opening. A user (e.g., a technician) may contact the first container (e.g., a substantially cylindrical side wall thereof, as opposed to the top or bottom of the first container) with first and second digits while the first container is located in the first opening. More particularly, while the first container is in the first opening, the user may contact the first container such that at least a portion of his/her first digit is located in a first gap between the first and second wings of the lid, and at least a portion of his/her second digit is located in a second gap between the first and second wings of the lid that is separate and distinct from the first gap.

In some embodiments of the fourth aspect, the contacting may further include the first digit being located within a first recess defined in the lid, and the second digit may be located within a second recess defined in the lid. The first recess may be separate and distinct from the second recess. An interior of the second container may be at least partially evacuated. The non-radioactive medical fluid in the first container may include saline. The method may further include drawing the non-radioactive medical fluid from the first container, through the radioisotope generator, and into the second container after the inserting of the first container and the inserting of the second container. The non-radioactive medical fluid elutes a radioisotope as it flows through the radioisotope generator so that it includes the radioisotope prior to entering into the second container. The inserting of the second container may occur while the first container is in the first opening.

Various refinements exist of the features noted in relation to the above-mentioned aspects of the present disclosure. Further features may be incorporated in the above-mentioned aspects of the present disclosure as well. These refinements and additional features may exist individually or in any combination. For instance, various features discussed below in relation to any of the illustrated embodiments of the present disclosure may be incorporated into any of the above-described aspects of the present disclosure, alone or in any combination.

DETAILED DESCRIPTION OF THE ILLUSTRATED EMBODIMENTS

Figure 1:
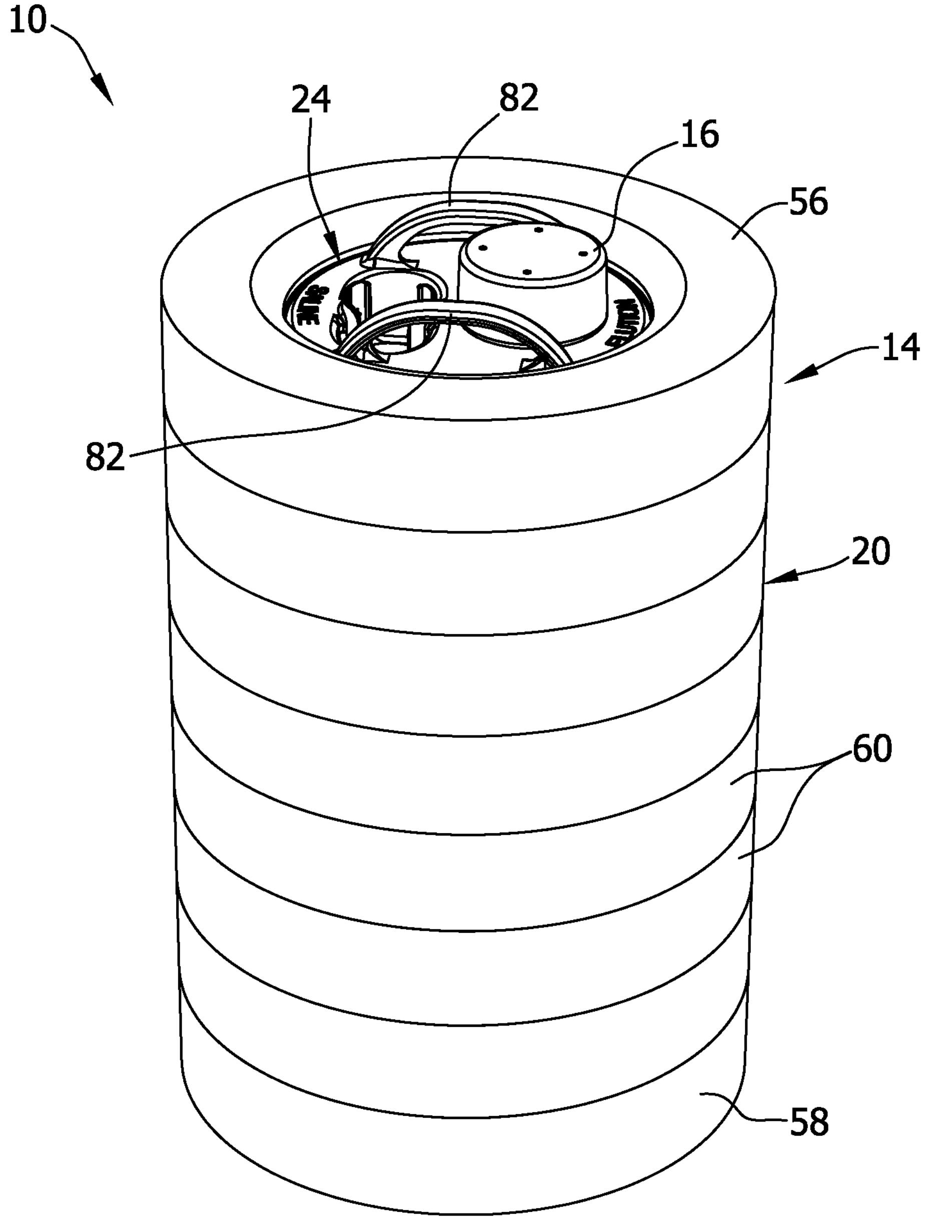
FIG. 1 is a perspective of one embodiment of a radioisotope elution system.
Figure 2:
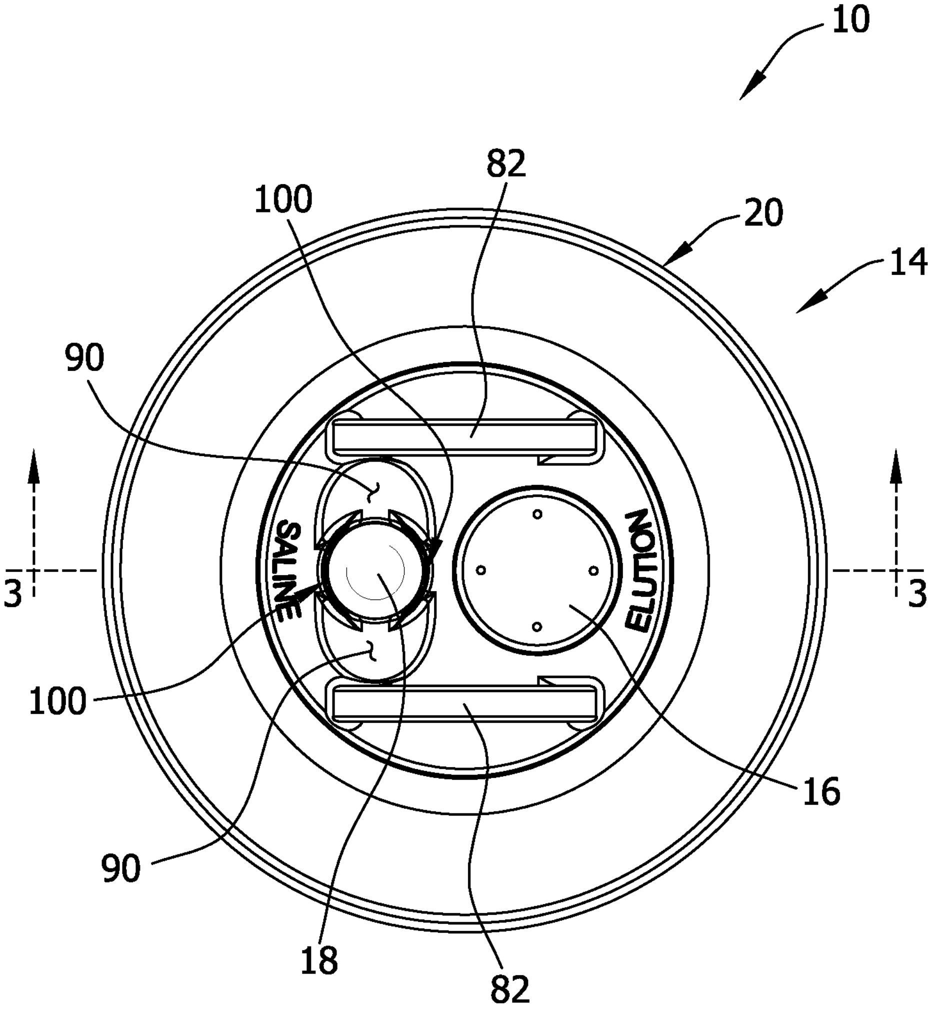
FIG. 2 is a top plan view of the radioisotope elution system of FIG. 1.

Referring to FIGS. 1-4, one embodiment of a radioisotope elution system 10 includes a radioisotope generator 12 (FIGS. 3 and 4), which is removably receivable in an auxiliary shield assembly 14. As explained in more detail below, an elution tool 16, which houses an elution vial 17 (broadly, a container), and an eluant vial 18 (broadly, a container) are fluidly connectable to the radioisotope generator 12. Herein, “fluidly connectable” refers to the ability of first component and a second component to be connected (either directly or indirectly) or interface in a manner such that fluid (e.g., eluate, eluant) may flow therebetween in a substantially confined flow path. The auxiliary shield assembly 14 includes a radiation shielding body 20 that defines a cavity 22 in which the generator 12 is removably receivable, and a radiation shielding lid 24 that may be positioned on the body 20 toward a top thereof to substantially enclose the cavity 22 defined in the body 20. In general, the radiation shielding lid 24 facilitates proper alignment of the eluant vial 18 with the radioisotope generator 12 when fluidly connecting the eluant vial with the radioisotope generator. Additional disclosure of the radiation shielding lid 24 is set forth in detail herein below.

The illustrated elution tool 16 may be of any appropriate configuration (e.g., size, shape, design), as is known to one having ordinary skill in the art, and may include one or more suitable radiation shielding materials, such as depleted uranium, tungsten, tungsten impregnated plastic, or lead. The illustrated elution vial 17 is a generally cylindrical container, made from glass or other material (e.g., plastic), which includes a septum (not shown) secured to a top portion thereof by a metal ring or cap (not shown), as is generally known in the art. The elution vial 17 may be a different type of container suitably connectable to a radioisotope generator and/or may have a shape other than generally cylindrical. In one embodiment, the interior of the elution vial 17 is at least partially evacuated such that the elution vial has a reduced internal pressure (i.e., at least a partial vacuum). The eluant vial 18, like the elution vial 17, may be a generally cylindrical container, which includes a septum (not shown) secured to a top portion thereof by a metal ring or cap (not shown), as is generally known in the art. The eluant vial 18 may be a different type of container suitably connectable to a radioisotope generator and/or may have a shape other than generally cylindrical. The eluant vial 18 is filled with an eluant fluid, such as saline. In one embodiment, the volume of eluant fluid is less than the volume of the elution vial 17. In another embodiment, the interior volume of eluant vial 18 is less than the interior volume of the elution vial 17. For example, the eluant vial 18 may have an internal volume of about 26 milliliters, and the interior volume of the elution vial 17 may be about 36 milliliters. The elution vial 17 and/or the eluant vial 18 may be of other configurations without departing from the scope of the present disclosure.

Figure 3:
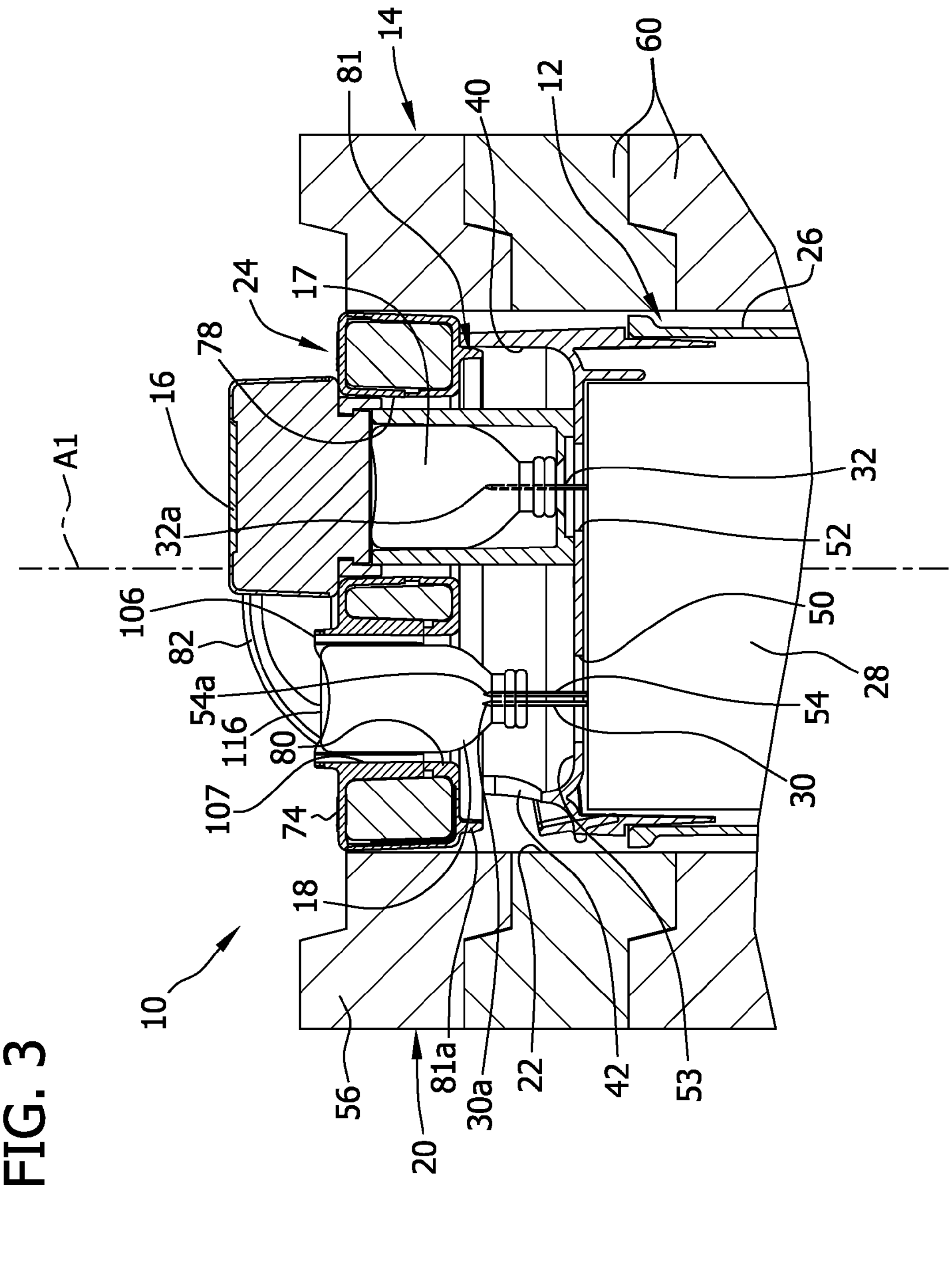
FIG. 3 is a cross section of the radioisotope elution system of FIG. 1 taken along line 3-3 in FIG. 2.
Figure 4:
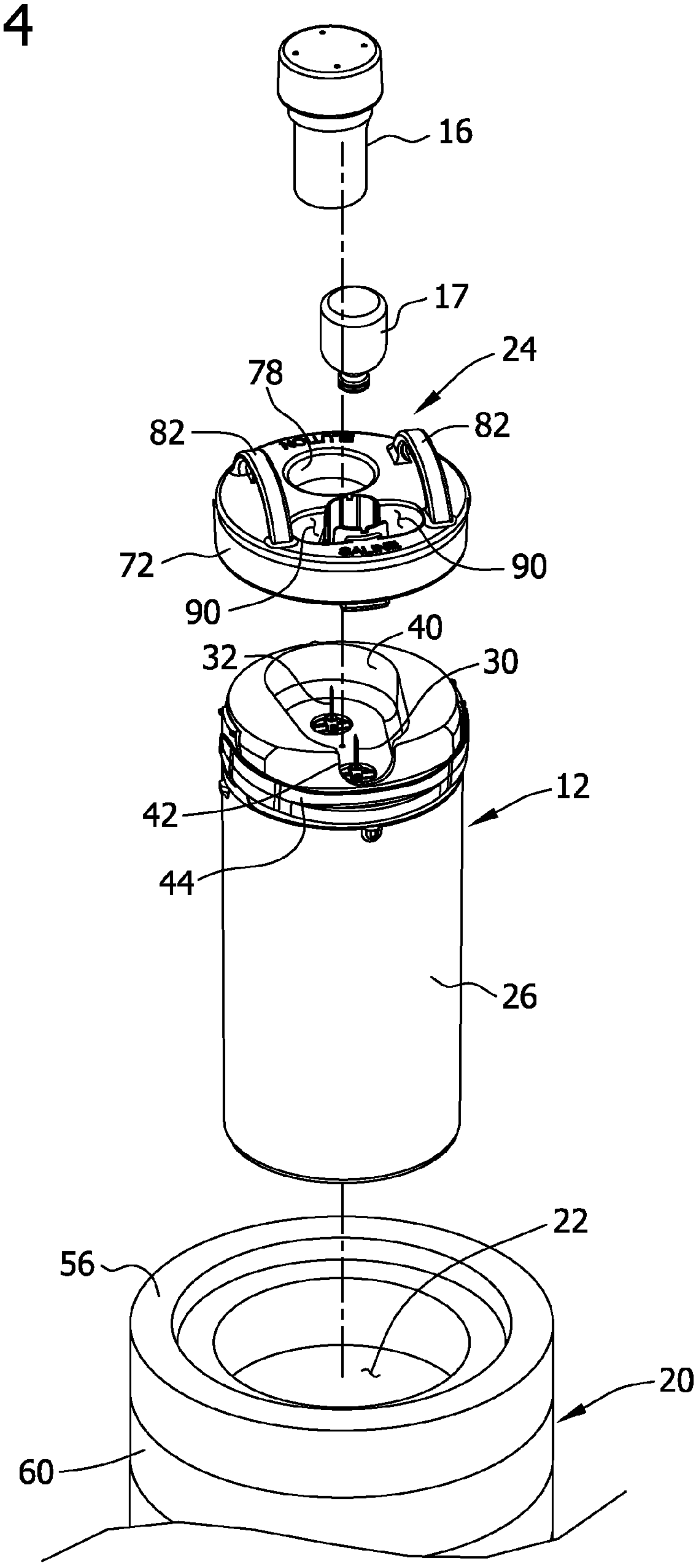
FIG. 4 is an exploded view of the radioisotope elution system of FIG. 1.
Figure 5:
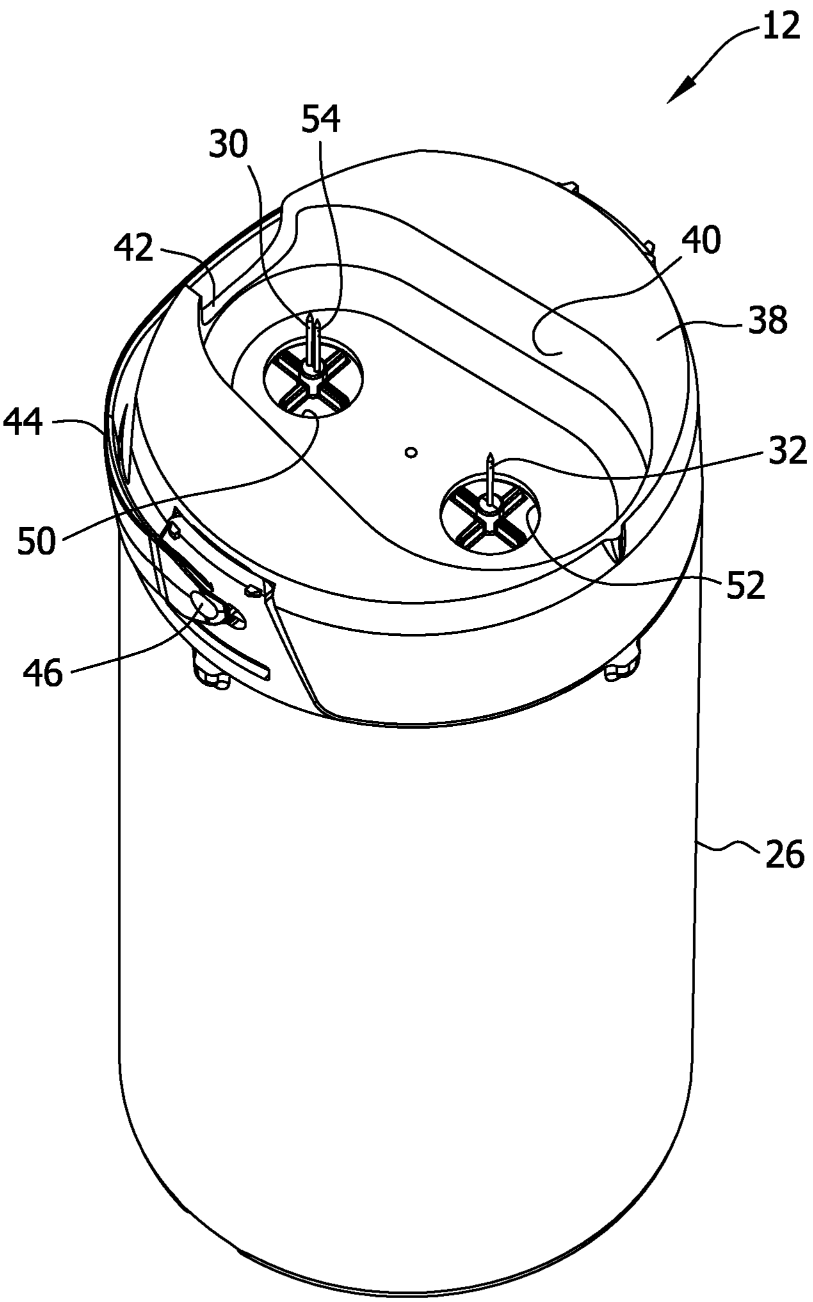
FIG. 5 is an enlarged perspective of a radioisotope generator of the radioisotope elution system of FIG. 1.
Figure 6:
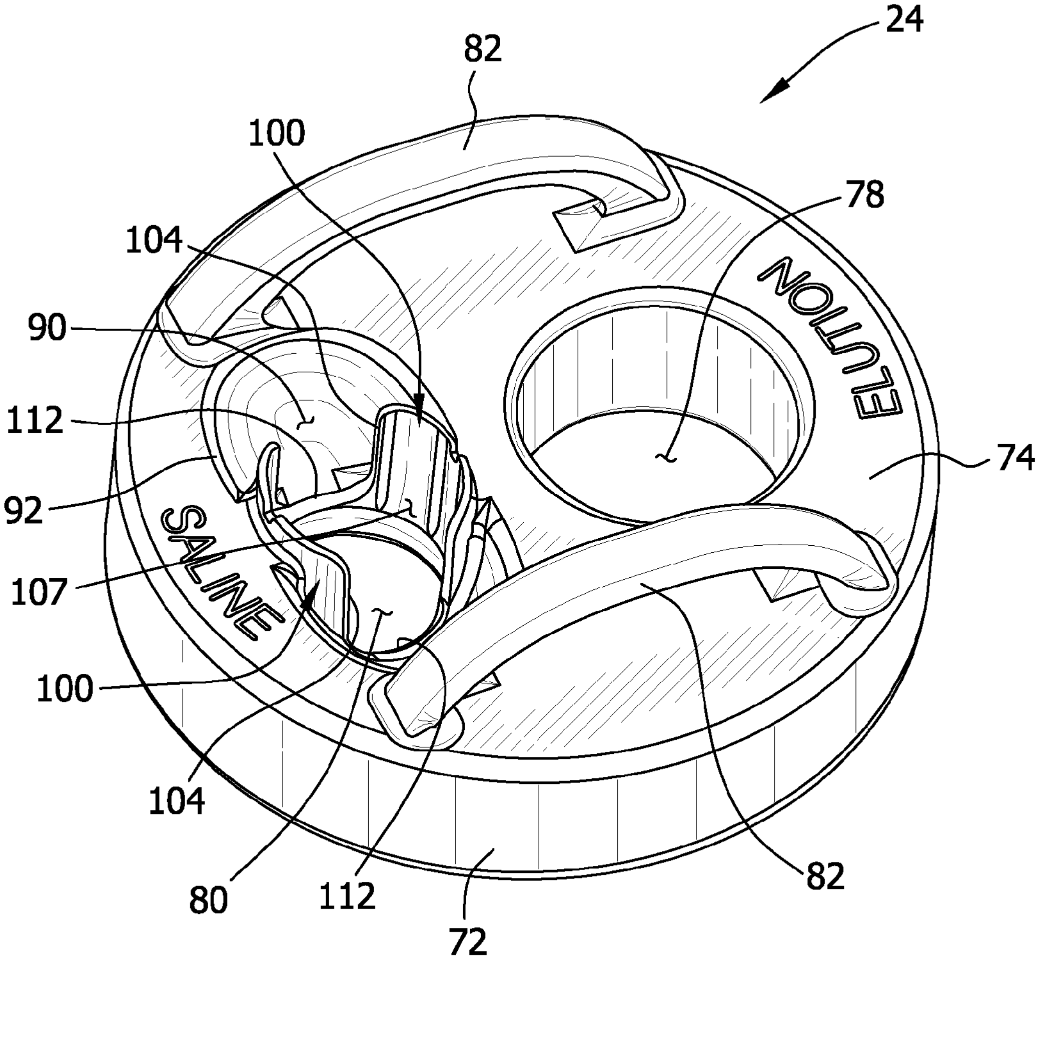
FIG. 6 is an enlarged perspective of an auxiliary shield assembly lid of the radioisotope elution system of FIG. 1.
Figure 7:
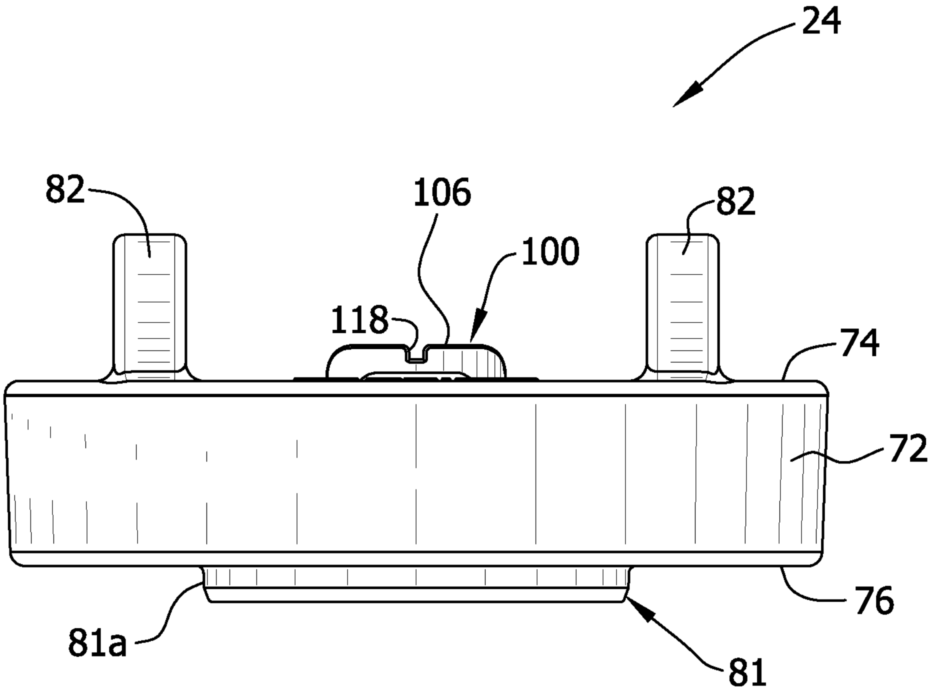
FIG. 7 is a front elevation of the auxiliary shield assembly lid of FIG. 6.

Referring to FIGS. 3-5, the radioisotope generator 12 includes: a housing 26; an elution column assembly 28 (FIG. 3) disposed within the housing; and input and output connectors 30, 32, respectively, in fluid communication with the elution column assembly 28; and a hood or cap 38 secured to the housing. The generator housing 26 is generally cylindrical and defines an axially extending cavity in which the elution column assembly 28 is received. The housing cap 38 may be snap-fit on the housing 26, or secured thereto in any other appropriate manner. The housing cap 38 has a recessed portion 40 extending downward from an upper surface of the cap. The cap 38 also has a generally U-shaped channel 42 extending downward from the upper surface and through a sidewall of the cap to the recessed portion 40. As explained in more detail below, the recessed portion 40 and the channel 42 together constitute an alignment structure, more specifically female alignment structure, for facilitating proper alignment of the radiation shielding lid 24 on the generator 12. The generator housing 26 and cap 38 may be formed from plastic (such as by molding) or from other suitable, preferably lightweight, material. Moreover, the generator housing 26 itself may be free from lead, tungsten, tungsten impregnated plastic, depleted uranium, or other radiation shielding material, such that the housing provides little or only nominal radiation shielding.

The generator 12 includes a generator handle 44 pivotally secured to the cap 38. The handle 44 is pivotable between a stored position, in which the handle lies in a plane substantially transverse to the axis A1 of the housing 26 (FIG. 3) and below the upper surface of the cap 38, and a carrying position, in which the handle lies in a plane substantially parallel to the axis of the housing and above the upper surface of the cap. The generator handle 44 allows a radiopharmacist or technician to lift the generator 12 for placement of the generator in the auxiliary shield assembly 14 and removal of the generator from the auxiliary shield assembly. The generator handle 44 may be formed from plastic or any other appropriate material and may be pivotally connected to the generator housing 26 by pivot connectors 46 (FIG. 5) or in any other appropriate manner of connection.

Referring to FIG. 3, the input and output connectors 30, 32 extend upward from the elution column assembly 28 and through respective openings 50, 52 in a bottom surface 53 of the recessed portion 40 of the generator cap 38 such that respective terminal ends or tips 30*a*, 32*a* of the input and output connectors are disposed within the recessed portion. In the illustrated embodiment, the input and output connectors 30, 32 respectively include input and output needles for piercing respective septums of the elution vial 17 and the eluant vial 18, although it is contemplated that the connectors may be of other configurations/types. In addition to the input and output connectors 30, 32, a venting connector 54, in fluid communication with atmosphere, extends through the bottom surface 53 of the recessed portion 40 of the cap 38. The venting connector 54 is adjacent to the input connector 30 and extends through the same opening 50 in the generator cap 38. In the illustrated embodiment, the venting connector 54 includes a venting needle having a terminal end or tip 54*a* disposed within the recessed portion 40 of the generator cap 38. The venting needle 54 pierces the septum of the eluant vial 18, like the input needle 30, to vent the eluant vial 18 to atmosphere.

Referring to FIG. 3, the elution column assembly 28 may be any appropriate type of elution column assembly known to those having ordinary skill in the art, such as, the elution column assembly disclosed in U.S. Pat. No. 5,109,160 or the elution column assembly found in the Ultra-Technekow™ dry-top eluting (DTE) generator distributed by Mallinckrodt LLC. For example, the elution column assembly 28 may include a radioactive column (not shown) including source of radioactive material (e.g., molybdenum-99, adsorbed to the surfaces of beads of alumina or a resin exchange column), and input and output conduits (not shown) fluidly connecting the input needle 30 to the column and the output needle 32 to the column. The elution column assembly 28 may include a column radiation shield (not shown) having a cavity in which the radioactive column is received, and a conduit radiation shield (not shown) surrounding the input and output conduits. The respective radiation shields may include (e.g., be made from or have in their construct) lead, tungsten, tungsten impregnated plastic, depleted uranium and/or another suitable radiation shielding material.

Referring back to FIG. 1, the illustrated auxiliary shield assembly body 20 includes a top ring 56, a base 58, and a plurality of step-shaped or generally tiered, modular rings 60, which are disposed one over the other between the base 58 and the top ring 56. Substantially all or part of the illustrated auxiliary shield assembly body 20 may be made of one or more suitable radiation shielding materials, such as depleted uranium, tungsten, tungsten impregnated plastic, or lead. The modular aspect of the rings 60 may tend to enhance adjustment of the height of the auxiliary shield assembly body 20, and the step-shaped configuration may tend to contain some radiation that might otherwise escape through a linear interface between the modular rings. It is understood that the auxiliary shield assembly body 20 may be of other configurations.

Referring now to FIGS. 6-11, the radiation shielding lid 24 includes: a generally cylindrical lid body 72 having upper and lower surfaces, 74, 76, respectively; an elution tool opening 78; and an eluant vial opening 80. In one example (of which an exemplary method of making is explained in more detail below), the lid body 72 includes a radiation shielding core 124 that is overmolded with a plastic material 126, 128. As an example, the radiation shielding core 124 may include depleted uranium, tungsten, tungsten impregnated plastic, or lead. The upper and lower surfaces 74, 76, respectively, are generally planar, although the surfaces may be other than generally planar.

A male alignment structure, generally indicated at 81, is provided on the lower surface 76 of the lid body 72 to facilitate proper alignment of the lid 24 on the generator 12. More specifically, the male alignment structure 81 has a shape generally corresponding with the combined shape of the recessed portion 40 and the channel 42 of the generator 12 (together, these recessed portion 40 and the channel 42 constitute a female alignment structure) so that the male alignment structure mates with the generator in order to align the elution tool opening 78 with the output needle 32 and the eluant vial opening 80 with the input needle 30 and the venting needle 54. As such, it may be said that the lid 24 is keyed with the generator 12 (e.g., the cap 38 thereof) such that proper positioning of the lid 24 atop the generator 12 results in alignment of the respective openings 78, 80 with the corresponding needles 32, 30. The structure 81 enables only one position of the lid 24 relative to the generator 12. The illustrated male alignment structure 81 includes a wall 81*a* projecting outward from the bottom surface 76 and surrounding the elution tool opening 78 and the eluant vial opening 80. A plurality (e.g., a pair) of handles 82 on the upper surface 74 of the lid body 72 allows the radiopharmacist or technician to properly place the lid 24 on the generator 12 and remove the lid from the generator.

The elution tool opening 78 extends through the lid body 72 from the upper surface 74 through the lower surface 76 thereof. The elution tool opening 78 is sized and shaped for removably receiving the elution tool 16 therein. For example, in the illustrated embodiment, the elution tool opening 78 has a generally circular circumference that is substantially uniform along its axis. In one embodiment, the elution tool opening 78 has a diameter slightly larger than an outer diameter of the elution tool 16 such that the opening effectively aligns the septum (not shown) of the elution vial 17 (FIG. 4) with the output needle 32 as the elution tool is inserted into the opening. For example, the elution tool opening 78 may have a diameter that is from about 0.25 mm (0.01 in) to about 1.0 mm (0.04 in) larger than the outer diameter of the elution tool 16. In one embodiment, the elution tool opening 78 may have a diameter from about 46 mm (1.8 in) to about 48 mm (1.9 in), although it may alternatively have a diameter falling outside this range. Other shapes and sizes of the elution tool opening 78 may be appropriate; however, it tends to be preferred that the shape and size of the elution tool opening 78 be at least generally complimentary to the shape and size of the elution tool 16 being used with the radiation shielding lid 24 to reduce the likelihood of misalignment between the elution vial 17 and the output needle 32.

Figure 9:
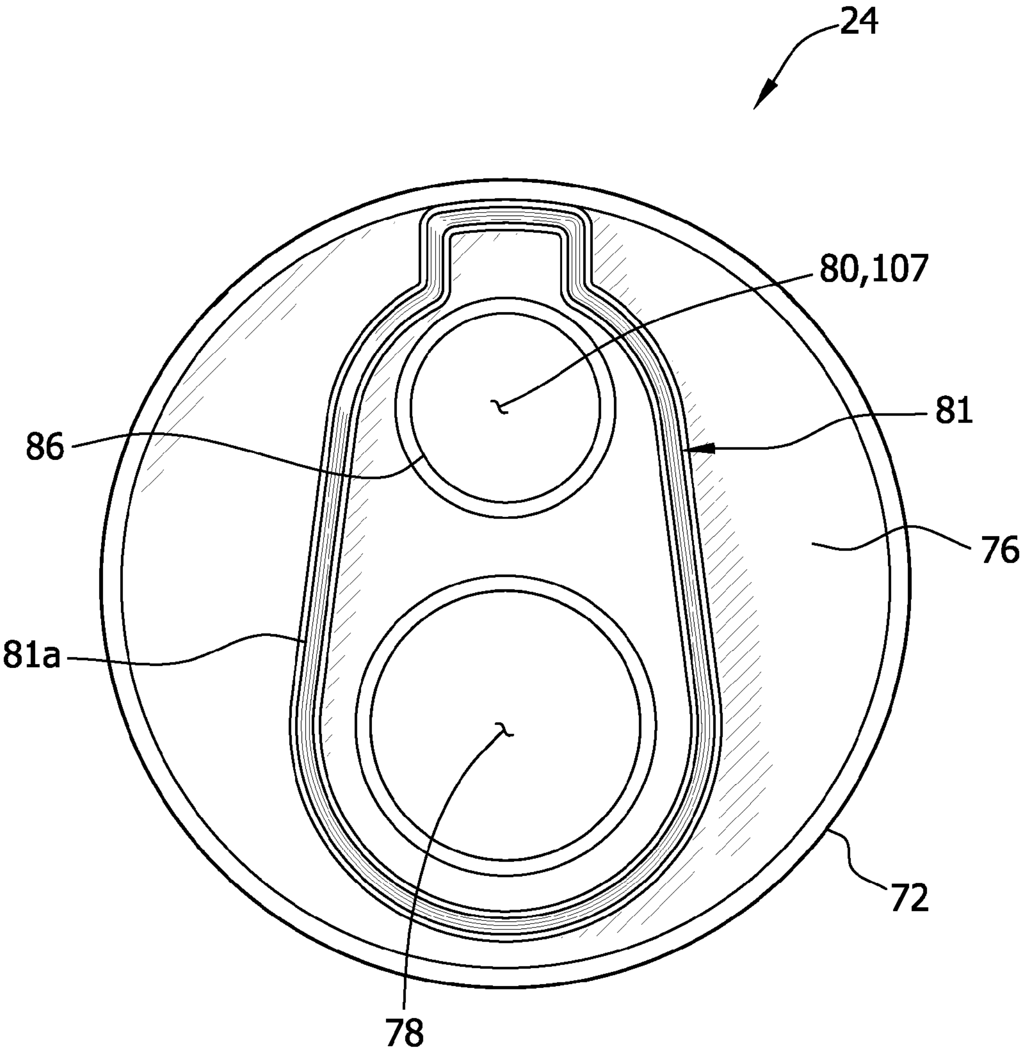
FIG. 9 is a bottom plan of the auxiliary shield assembly lid of FIG. 6.
Figure 10:
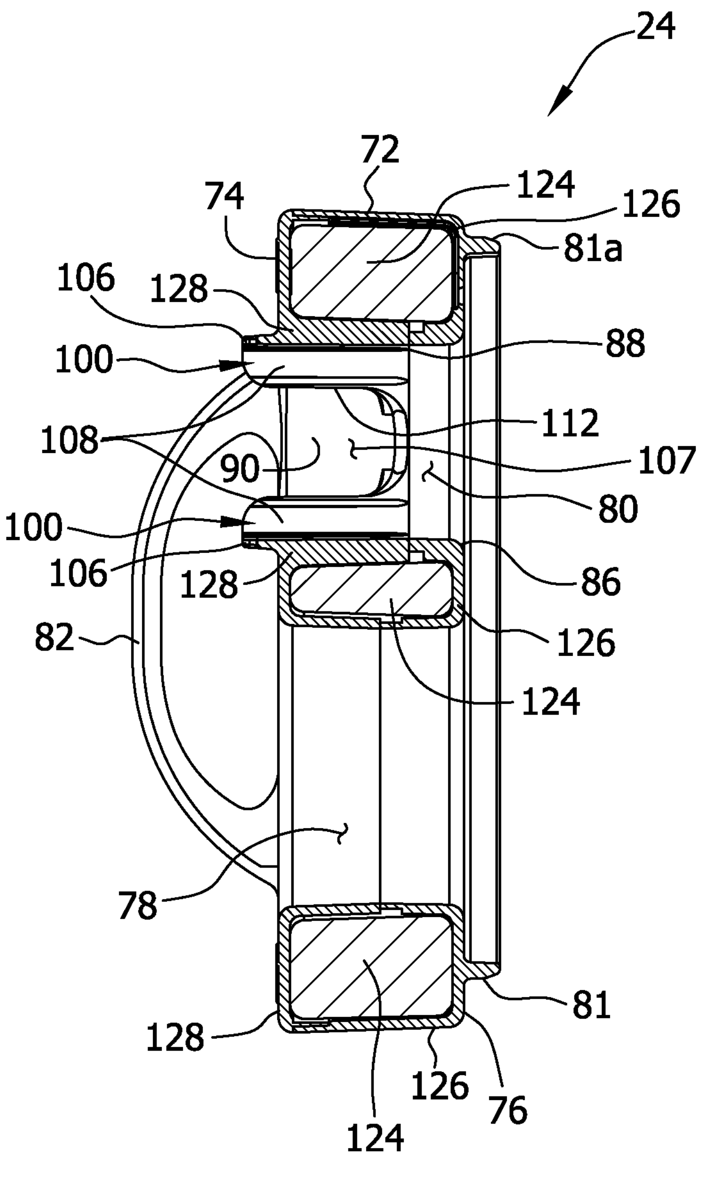
FIG. 10 is a cross section of the auxiliary shield assembly lid of FIG. 6 taken through line 10-10 in FIG. 8.

As shown in FIGS. 9 and 10, the eluant vial opening 80 is spaced apart and separate from the elution tool opening 78, and is sized and shaped for removably receiving an eluant vial 18 (FIG. 2), such as a vial containing saline or other eluants.

In the illustrated embodiment (FIG. 10), the eluant vial opening 80 has a lower end 86 at the lower surface 76 of the lid body 72 and an upper end 88 intermediate the upper and lower surfaces 74, 76, respectively. In one example, the eluant vial opening 80 may have a diameter from about 34.0 mm (1.34 in) to about 34.5 mm (1.36 in), although it may alternatively have a diameter falling outside this range. As with the elution tool opening 78, other shapes and sizes of the eluant vial opening 80 may be appropriate; however, it tends to be preferred that the shape and size of the eluant vial opening 80 be at least generally complimentary to the shape and size of the eluant vial 18 being used with the radiation shielding lid 24 to reduce the likelihood of misalignment between the eluant vial 18 and the input needle 30 and venting needle 54.

Figure 8:
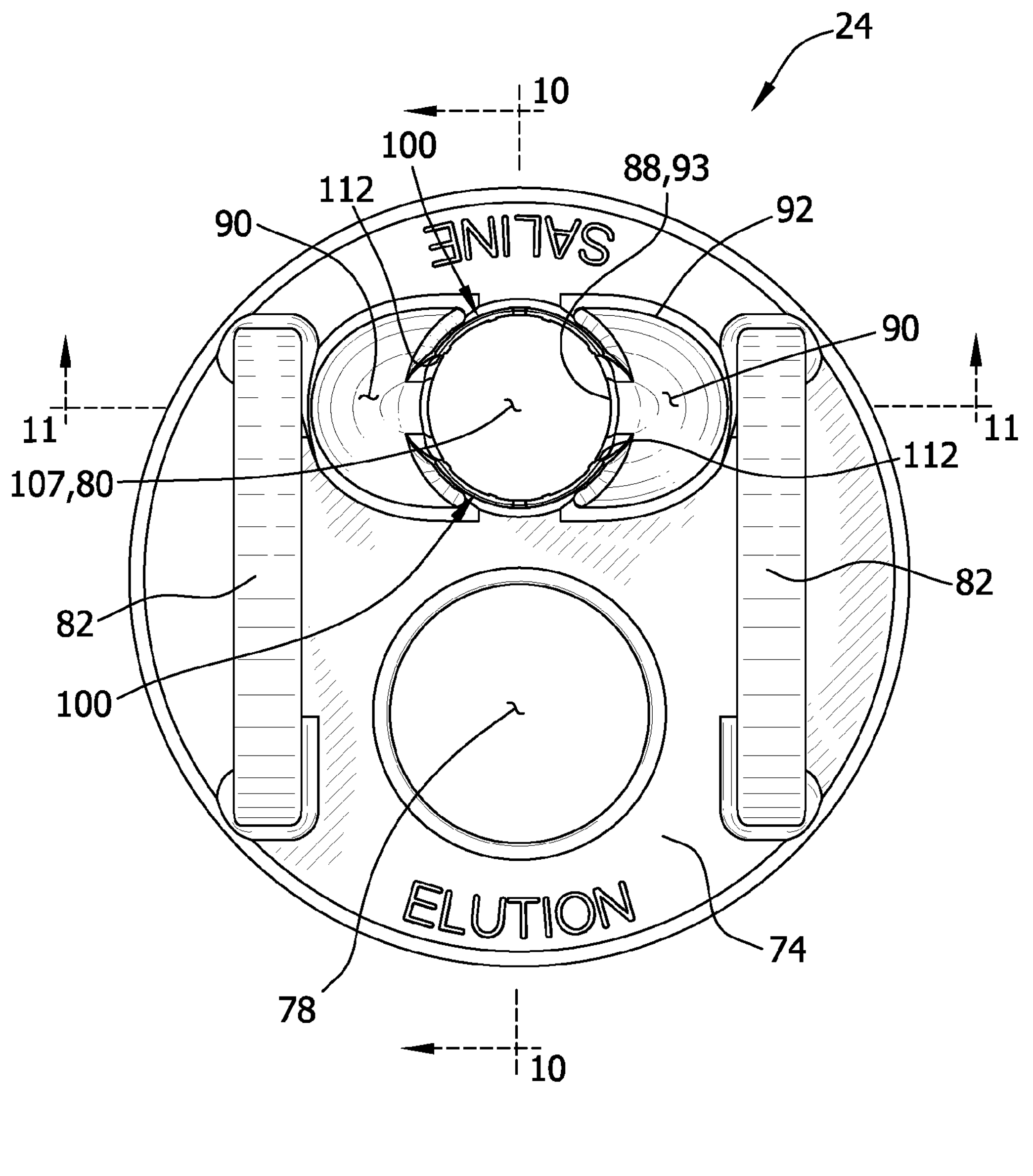
FIG. 8 is a top plan of the auxiliary shield assembly lid of FIG. 6.

Referring to FIGS. 2, 6, 8, and 11, the illustrated lid 24 has two finger recesses 90 formed in the upper surface 74 of the lid body 72, which are diametrically opposite one another with respect to the eluant vial opening 80. The finger recesses 90 are defined by respective recessed surfaces extending downward from the upper surface 74 of the lid body 72 to the eluant vial opening 80, and are sized and shaped to allow at least distal portions of two fingers of a radiopharmacist or other appropriate technician to enter the finger recesses. Recessed surfaces defining illustrated finger recesses 90 are curved and generally in the shape of a half-bowl such that the recessed surfaces lead the radiopharmacist's or technician's fingers toward the eluant vial opening 80. It is understood that in other embodiments the lid 24 may have a single finger recess, such as a finger recess that completely or partially surrounds the eluant vial opening 80, or more than two finger recesses. Referring to FIG. 8, each illustrated finger recess 90 has an upper edge 92 adjacent the upper surface 74 of the lid body 72 and a lower edge 93 that is coextensive with a portion of the upper end 88 of the eluant vial opening 80.

Figure 11:
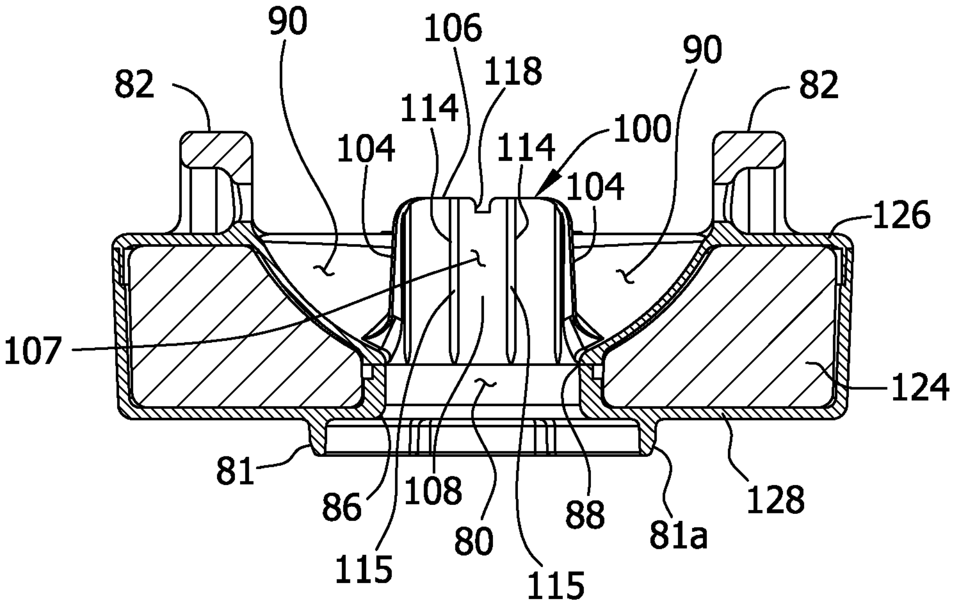
FIG. 11 is a cross section of the auxiliary shield assembly lid of FIG. 6 taken through line 11-11 in FIG. 8.

Referring to FIG. 11, the lid 24 of the auxiliary shield assembly 14 includes first and second wings, each designated generally at reference numeral 100, extending upward from adjacent the upper end 88 of the eluant vial opening 80 within the finger recesses 90. Each of the first and second wings 100 has opposite sides 104, a top portion 106, and an inner surface 108 extending partially around a circumference of the upper end 88 of the eluant vial opening 80. In the illustrated embodiment, the top portion 106 of each of the wings 100 is disposed above the upper surface 74 of the lid body 72 (as seen best in FIGS. 7 and 10), and the inner surface 108 of each of the wings 100 is generally arcuate, although it is understood that the wings 100 may be of other shapes and relative dimensions. Together, the inner surfaces 108 of the wings 100 and the eluant vial opening 80 define a vial passageway 107 extending from the top portions 106 of the wings 100 through the lower surface 76 of the lid body 72.

The wings 100 preferably enable alignment of the eluant vial septum with the input needle 30 and venting needle 54 as the eluant vial 18 is inserted into the vial passageway 107. As such, the wings 100 preferably make it is less likely that the input needle 30 or venting needle 54 will contact the metal ring or other hard part of the vial and damage the needle. In one example, the inner surface 108 of each wing 100 may extend at least 45 degrees and less than 180 degrees around the circumference of the upper end 88 of the eluant vial opening 80. In other examples, the inner surface 108 of each wing 100 may extend at least 60 degrees, or at least 90 degrees, and less than 180 degrees around the circumference of the upper end 88 of the eluant vial opening 80. Other configurations of the wings 100 do not depart from the scope of the present disclosure.

To facilitate gripping of the eluant vial 18 during at least one of insertion of the vial into the vial passageway 107 and removal of the vial from the vial passageway, the respective adjacent sides 104 of the first and second wings 100 are spaced apart from one another about the eluant vial opening 80 to define gaps or first and second finger channels, each indicated at 112 (FIGS. 6 and 10), leading from the finger recesses 90 to the vial passageway. In the illustrated embodiment, the finger channels 112 are diametrically aligned, relative to the vial opening 80, with the finger recesses 90, and the respective sides 104 of the wings 100 extend into the associated finger recesses 90. Each of the first and second finger channels 112 are sized and shaped to allow at least the distal portion of one of the two fingers to enter the corresponding finger channel from the associated finger recess 90. For example, a minimum width of each of the finger channels 112 (i.e., the distance between the respective adjacent sides 104 of the first and second wings 100) may measure from about 19 mm (0.75 in) to about 21 mm (0.83 in), and more specifically, from about 19.0 mm (0.748 in) to about 19.6 mm (0.772 in), although the minimum width of each finger channel may fall outside this range. Thus, the finger channels 112 allow the radiopharmacist or technician to grip the eluant vial 18, such as by using his/her thumb and forefinger, during at least one of insertion of the vial in the vial passageway 107 and removal of the vial from the vial passageway.

In the illustrated embodiment (FIGS. 8, 10, and 11), a diameter of a portion of the vial passageway 107 defined by the inner surfaces 108 of the wings 100 tapers from the top portions 106 of the wings toward the eluant vial opening 80. Tapering the inner surfaces 108 of the wings 100 facilitates molding of the wings when overmolding the lid 24 in one example, as described below. Although this diameter of the vial passageway 107, as defined by the inner surfaces 108, tapers along the length of the passageway, a plurality of alignment ribs 114 are provided on the inner surfaces to define an effective inner diameter of the vial passageway that is substantially uniform along the length of the passageway. The ribs 114 are spaced apart from one another between the sides 104 of the wings and extend longitudinally along the respective wings 100. The wings 100 project inwardly, generally toward a centerline of the passageway 107, such that each rib 114 has a terminal, guiding surface 115 (FIG. 11) generally facing the centerline of the passageway. Each guiding surface 115 is uniformly spaced from the centerline of the vial passageway 107 along its length. In other words, the guiding surface 115 of each rib 114 does not taper or flare with respect to the axis of the vial passageway 107. Through this configuration, the guiding surfaces 115 effectively align the elution vial 18 with the input needle 30 and venting needle 54 even though the inner surfaces 108 of the wings 100 are tapered. The ribs 114 have depths projecting into the vial passageway 107 relative to the respective inner surfaces 108. Because the diameter of the vial passageway 107 defined by the inner surfaces 108 of the wings 100 tapers, yet the guiding surfaces 115 do not taper or flare relative to the centerline of the vial passageway, the depths of the ribs relative to the respective inner surfaces 108 taper toward the eluant vial opening 80. The wings 100 may not include the ribs 114 without departing from the scope of the present disclosure.

As illustrated in FIG. 3, a bottom 116 of the eluant vial 18 lies slightly below or at the top portions 106 of the wings 100 when the eluant vial is received in the vial passageway 107 and fluidly connected to the input needle 30. Notches 118 in the top portions 106 of the wings 100 allow the radiopharmacist or technician to view the eluant vial 18 in the passageway without having to position his/her head above the upper surface 74 of the lid 24.

In one example, the auxiliary shield lid 24 may be formed by a two-step overmolding process. In such a process, a radiation shielding core 124 (FIG. 10)—which may include a suitable radiation shielding material such as depleted uranium, tungsten, tungsten impregnated plastic, or lead—is provided. The core 124 may be generally disk-shaped, having first and second openings, which will form the elution tool and eluant vial openings, 78, 80, respectively, and recesses, which will form the finger recesses 90. A first molded part is molded with a first thermoplastic material 126 to form the bottom surface 76, the male alignment structure 81, and the sidewall of the body 72, and at least lower portions of the elution tool opening 78 and the eluant vial opening 80. Next, the core 124 is placed into the first molded part. Finally, this assembly is overmolded with a second thermoplastic material 128 to form the top surface 74, the handles 82, the finger recesses 90, the wings 100, and an upper portion of at least the elution tool opening 78. The first and second thermoplastic materials 126, 128, respectively, may include polypropylene and polycarbonate, or other material, and the first and second thermoplastic materials may be of the same material. Other methods of making the auxiliary shield lid 24 may be used.

In an exemplary method of using the radioisotope elution system 10, the radiopharmacist or technician manually inserts the radioisotope generator 12 into the cavity 22 of the auxiliary shield body 20. The auxiliary shield lid 24 is manually placed in the cavity, on top of the radioisotope generator 12. The lid 24 may be rotated to thereby mate the male alignment structure 81 on the lid with the female alignment structure (i.e., the recessed portion 40 and the U-shaped channel 42) in the cap 38 of the generator 12. Upon mating, the eluant vial opening 80 is disposed over and generally vertically aligned with the input needle 30 and the venting needle 54, and elution tool opening 78 is disposed over and generally vertically aligned with the output needle 32. The eluant vial 17 is manually inserted into the passageway defined by the wings 100 and the eluant vial opening 80. The passageway guides the eluant vial 17 in a substantially vertical direction, such that the longitudinal axis of the eluant vial is generally aligned with the axes of the input needle 30 and the venting needle 54. More specifically, the passageway guides the eluant vial 17 such that the input needle 30 and the venting needle 54 pierce the septum of the vial to fluidly connect the interior of the eluant vial to the generator 12. Accordingly, the wings 100 give the radiopharmacist or technician confidence that the input needle 30 and venting needle 54 will pierce the septum, and therefore, the radiopharmacist or technician does not have to position his/her head directly above the lid 24 to confirm that the needles will properly pierce the eluant vial septum. To this effect, the radiopharmacist or technician reduces any likelihood of radiation exposure from the generator 12 when positioning his/her head over the eluant vial opening 80.

The elution tool 16, which includes the elution vial 17 therein, is manually inserted into the elution tool opening 78 such that the output needle 32 pierces the septum of the elution vial to fluidly connect the elution vial to the generator 12. The vacuum (or reduced pressure) in the elution vial 17 draws the saline from the vial 18 through the radioisotope column and into the elution vial 17. The radiopharmacist or technician can view the bottom 116 of the eluant vial 18 through the notches 118 in the respective wings 100 when the vial is received in the passageway 107 to confirm that the eluant vial 18 is fully inserted onto the generator 12. Accordingly, the radiopharmacist or technician does not have to position his/her head directly above the lid 24 to confirm that the needles 30, 54 actually pierced the eluant vial septum. Once confirmation is made that the vial is properly placed, an eluant vial shield (not shown) may be placed over the bottom of the eluant vial.

After the elution vial 17 is filled with the desired quantity of radioisotope-containing saline, the elution tool 16 can be manually removed from the lid 24. A vial (not shown) containing a sterile liquid may be placed on the output needle 32. The eluant vial 18 may remain on the radioisotope generator 12 until a subsequent elution in order to keep the needles 30, 54 sterile. When it is time for a subsequent elution, the eluant vial 18 can be manually removed from lid 24, such as by the radiopharmacist or technician inserting his/her thumb and forefinger into the respective finger recesses 90 and then into the respective finger channels 112 to grip (or pinch) the eluant vial. The radiopharmacist or technician can then lift the eluant vial 18 upward and out of the lid 24.

When introducing elements of the present invention or the embodiment(s) thereof, the articles "a", "an", the and "said" are intended to mean that there are one or more of the elements. The terms "comprising", "including" and "having" are intended to be inclusive and mean that there may be additional elements other than the listed elements.

As various changes could be made in the above apparatus and methods without departing from the scope of the disclosure, it is intended that all matter contained in the above description and shown in the accompanying figures shall be interpreted as illustrative and not in a limiting sense.

What is claimed is:

1. A radiation shielding lid for a radiation shielding container, the lid comprising:

a body having an upper surface and an opposing lower surface;

a vial opening defined in the body, the vial opening having a lower end at the lower surface of the body and an upper end intermediate the upper and lower surfaces of the body;

a finger recess in the upper surface of the body, the finger recess sized and shaped to allow at least distal portions of at least two digits to enter the finger recess, wherein the finger recess has an upper edge adjacent the upper surface of the body and a lower edge adjacent the upper end of the vial opening;

first and second wings extending upward from adjacent the upper end of the vial opening, each of the first and second wings having opposite sides, a top portion, and an inner surface extending partially around a circumference of the upper end of the vial opening;

wherein the inner surfaces of the first and second wings and the vial opening together define a vial passageway extending from the top portions of the first and second wings through the lower surface of the body, the vial passageway being sized and shaped for receiving a vial therein;

wherein respective adjacent sides of the first and second wings are spaced apart from one another around the vial opening to partially define first and second finger channels leading from the finger recess to the vial passageway, each of the first and second finger channels being sized and shaped to allow at least the distal portion of one of the two digits to enter the corresponding finger channel from the finger recess to facilitate gripping of the vial during at least one of insertion of the vial in the vial passageway and removal of the vial from the vial passageway.

2. The lid set forth in claim 1, wherein the inner surface of each of the first and second wings extends at least 45 degrees and less than 180 degrees around the circumference of the upper end of the vial opening.

3. The lid set forth in claim 2, wherein the top portions of the first and second wings extend above the upper surface of the body.

4. The lid set forth in claim 2, wherein the inner surface of each of the first and second wings extends at least 60 degrees around the circumference of the upper end of the vial opening.

5. The lid set forth in claim 4, wherein the inner surface of each of the first and second wings extends at least 90 degrees around the circumference of the upper end of the vial opening.

6. The lid set forth in claim 1, wherein the inner surfaces of the first and second wings are diametrically opposed to one another with respect the vial opening.

7. The lid set forth in claim 1, wherein the sides of the respective first and second wings extend into the finger recess.

8. The lid set forth in claim 1, wherein the finger recess comprises first and second finger recesses, wherein the first and second finger recesses are diametrically opposed to one another with respect to the vial opening.

9. The lid set forth in claim 8, wherein the lower edge of the first finger recess extends between the corresponding adjacent sides of the first and second wings to partially define the first finger channel, and wherein the lower edge of the second finger recess extends between the corresponding adjacent sides of the first and second wings to partially define the second finger channel.

10. The lid set forth in claim 1, wherein the top portions of the first and second wings extend above the upper surface of the body.

11. The lid set forth in claim 10, wherein at least one of the first and second wings has a notch in the corresponding top portion.

12. The lid set forth in claim 1, wherein the upper end of the vial opening is substantially circular, and wherein the inner surfaces of the first and second wings are generally arcuate.

13. The lid set forth in claim 1, wherein a portion of the vial passageway defined by the inner surfaces of the wings tapers from the top portions of the wings toward the vial opening.

14. The lid set forth in claim 1, wherein each of the first and second wings includes a plurality of ribs on the inner surface of each wing projecting inward into the vial passageway, the ribs on each wing being spaced apart from one another between the opposite sides of each wing.

15. The lid set forth in claim 14, wherein the ribs project generally toward a centerline of the passageway from the inner surface of the corresponding wing, such that each rib has a terminal, guiding surface generally facing a centerline of the vial passageway, wherein each guiding surface is uniformly spaced from the centerline of the vial passageway along its length.

16. The lid set forth in claim 1, wherein the body is substantially disk-shaped and is formed, at least in part, from a radiation shielding material comprising at least one of depleted uranium, tungsten, tungsten impregnated plastic, or lead.

17. The lid set forth in claim 1, further comprising an elution tool opening defined in the body, wherein the elution tool opening is spaced apart and separate from the vial opening.

18. A lid for a radiation shielding container comprising:

a body having upper and lower surfaces;

a vial opening in the body having a centerline extending through the upper and lower surfaces of the body, the vial opening being sized and shaped to allow insertion of a vial therein;

first and second alignment wings extending upward from the vial opening, each of the first and second alignment wings having opposite sides, a top portion, and an inner surface extending partially around a circumference of the vial opening;

wherein the first and second alignment wings enable alignment of a longitudinal axis of a vial with the centerline of the vial opening as the vial is inserted in the vial opening;

wherein respective adjacent sides of the first and second alignment wings partially define at least one finger channel, the at least one finger channel being sized and shaped to allow at least the distal portion of at least one digit to enter the finger channel to facilitate at least one of insertion of the vial in the vial opening and removal of the vial from the vial opening.

19. The lid set forth in claim 18, wherein the inner surface of each alignment wing extends at least 45 degrees and less than 180 degrees around the circumference of the vial opening, wherein said at least one finger channel comprises at least a first finger channel and a second finger channel.

20. The lid set forth in claim 19, further comprising first and second finger recesses in the upper surface of the body, each of the first and second finger recesses having an upper edge adjacent the upper surface of the body and a lower edge leading to the vial opening, wherein the first and second finger recesses are diametrically opposed to one another with respect to the vial opening.

21. The lid set forth in claim 18, further comprising an elution tool opening defined in the body, wherein the elution tool opening is spaced apart and separate from the vial opening.

* * * * *